(12) United States Patent
Guru et al.

(10) Patent No.: US 10,286,125 B2
(45) Date of Patent: May 14, 2019

(54) SUCTION DEVICE FOR NORMAL AND VISCOUS MATERIALS

(71) Applicant: Health Research, Inc., Buffalo, NY (US)

(72) Inventors: Khurshid Guru, East Amherst, NY (US); Ashirwad Chowriappa, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 779 days.

(21) Appl. No.: 14/776,074

(22) PCT Filed: Mar. 14, 2014

(86) PCT No.: PCT/US2014/029702
§ 371 (c)(1),
(2) Date: Sep. 14, 2015

(87) PCT Pub. No.: WO2014/145052
PCT Pub. Date: Sep. 18, 2014

(65) Prior Publication Data
US 2016/0022883 A1    Jan. 28, 2016

Related U.S. Application Data

(60) Provisional application No. 61/798,677, filed on Mar. 15, 2013.

(51) Int. Cl.
*A61M 1/00* (2006.01)
*A61B 17/00* (2006.01)
*A61B 17/32* (2006.01)

(52) U.S. Cl.
CPC ....... *A61M 1/008* (2013.01); *A61B 17/32002* (2013.01); *A61B 2017/00553* (2013.01);
(Continued)

(58) Field of Classification Search
CPC ............... A61M 1/008; A61M 1/0082; A61M 2206/20; A61B 17/32002;
(Continued)

(56) References Cited

U.S. PATENT DOCUMENTS 3,485,246 A * 12/1969 Austin, Jr. ............. A61C 17/04
417/198
4,649,919 A    3/1987 Thimsen
(Continued)

FOREIGN PATENT DOCUMENTS

WO    1993/025248    12/1993
WO    2005023354    3/2005

OTHER PUBLICATIONS

Krankenberg et al., Behandlung peripherer arterieller Thrombembolien durch ein neuartiges perkutanes mechanisches Thrombektomiesystem, Fortschr Rontgenstr 2001, 173: 236-239. Jan. 1, 2000.

*Primary Examiner* — Tatyana Zalukaeva
*Assistant Examiner* — Gabriella E Burnette
(74) *Attorney, Agent, or Firm* — Hodgson Russ LLP

(57) ABSTRACT

A device for removing viscous or semi-viscous material from an individual is disclosed. The device uses suction which may be provided by a vacuum source. The device includes a tube. The tube has a proximal opening and a distal opening, and a first stop at a first lengthwise position on an inner wall of the tube. The distal opening is in pneumatic communication with the vacuum source. The device also includes an agitator rotatably disposed in the tube. The agitator has a helical blade, a first end, and a second end. The first end is configured to engage the first stop such that the agitator is rotatable about the axis of the helical blade while being at a substantially fixed position along the length of the tube.

14 Claims, 16 Drawing Sheets

(52) U.S. Cl.
CPC ............ *A61B 2017/320024* (2013.01); *A61B 2217/005* (2013.01); *A61M 1/0082* (2014.02); *A61M 2206/20* (2013.01)

(58) Field of Classification Search
CPC ......... A61B 2017/00553; A61B 2017/320024; A61B 2217/005
See application file for complete search history.

(56) References Cited

U.S. PATENT DOCUMENTS

| | | | |
|---|---|---|---|
| 5,226,909 A * | 7/1993 | Evans | A61B 17/320783 604/22 |
| 5,571,081 A | 11/1996 | Adhoute | |
| 5,899,915 A | 5/1999 | Saadat | |
| 6,143,009 A * | 11/2000 | Shiber | A61B 17/320758 606/159 |
| 2002/0143350 A1 | 10/2002 | Heitzmann et al. | |
| 2002/0188280 A1 | 12/2002 | Nguyen | |
| 2012/0071907 A1 | 3/2012 | Pintor et al. | |

* cited by examiner

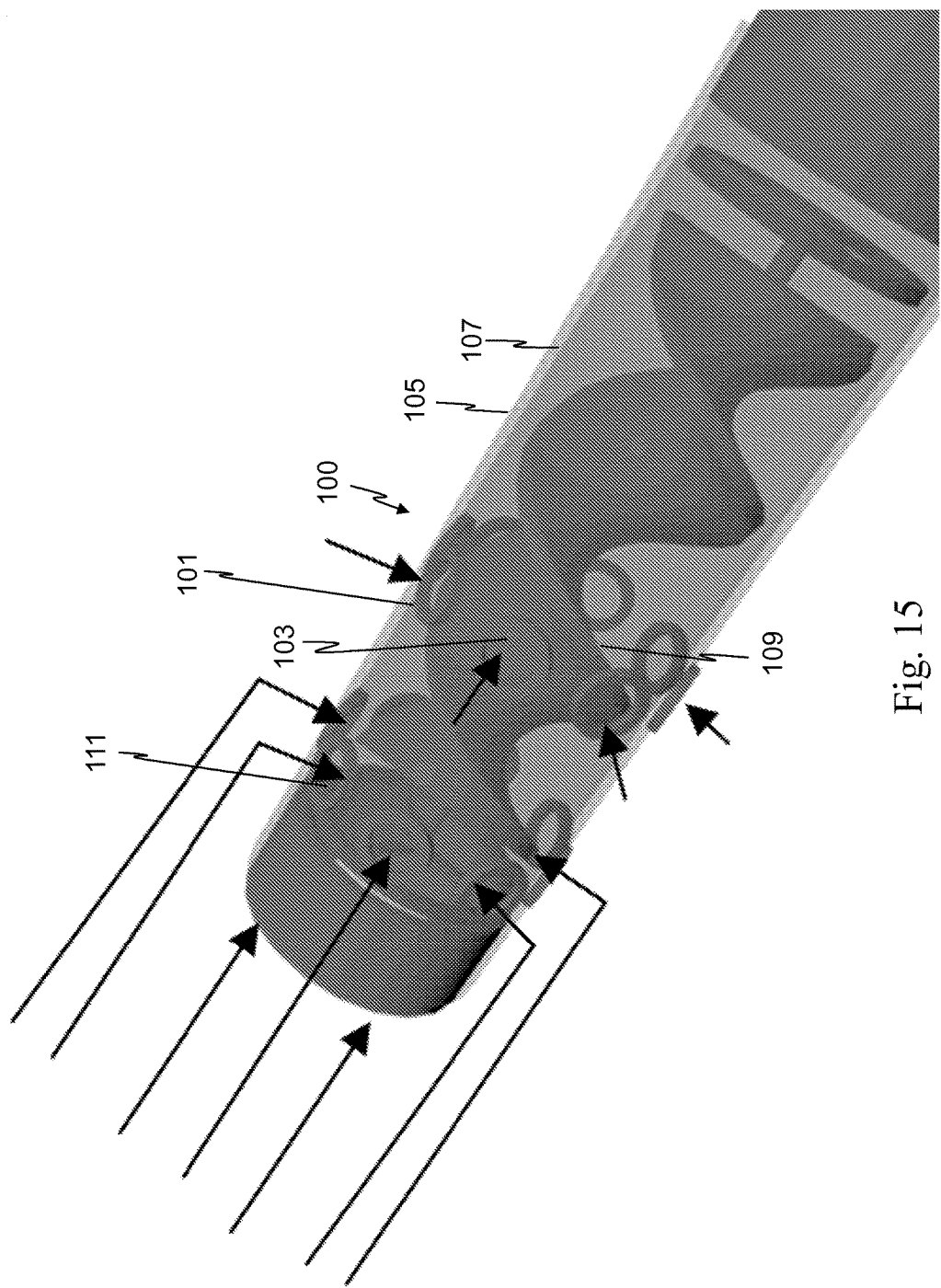

SUCTION DEVICE FOR NORMAL AND VISCOUS MATERIALS

CROSS-REFERENCE TO RELATED APPLICATIONS

This application claims priority to U.S. Provisional Application No. 61/798,677, filed on Mar. 15, 2013, the disclosure of which is incorporated by reference.

FIELD OF THE INVENTION

The invention relates to a suction device for normal and viscous material, such as, for example, an unpowered surgical suction device.

BACKGROUND OF THE INVENTION

Surgical aspirator cannulas and suction devices have been used for many years to remove fluid from the body. These suction devices typically comprise a hollow tube, or cannula, having an opening at each end. The distal opening (with respect to the patient) is attached to a source of vacuum. The opposite, proximal, end is introduced into the body and fluid is removed through the cannula by force of the suction. Typically, when a vacuum is provided from the vacuum source, the fluid is sucked into the opening on the proximal end of the tube, through the tube, and into a receptacle disposed "downstream" with respect to the tube. Such suction devices may become clogged, requiring cleaning of the suction devices. This frequently occurs during surgical procedures involving suction of viscous and/or non-viscous fluid.

BRIEF SUMMARY OF THE INVENTION

The present disclosure provides a device for removing viscous or semi-viscous material from an individual using suction. The suction may be provided by a vacuum source. The device comprises a tube and an agitator.

The tube has a proximal opening and a distal opening. The distal opening is in pneumatic communication with a vacuum source. The tube also has a first stop at a first lengthwise position on an inner wall of the tube. The first stop may be a collar affixed to the inner wall of the tube. In another embodiment, the first stop may be one or more protrusions. The protrusion may be formed by an indentation in the tube. In one embodiment, the first stop is sized to cover less than 20% of the circumference of the inner wall.

The agitator is rotatably disposed in the tube. The agitator has a helical blade, a first end, and a second end. The first end is configured to engage the first stop such that the agitator is rotatable about the axis of the helical blade while being at a substantially fixed position along the length of the tube. For example, the first end of the agitator may be configured as a ring. The ring may be connected to the helical blade by way of a connecting rod. The second end of the agitator may also be configured as a ring.

In one embodiment, the tube has a second stop at a second lengthwise position on the inner wall of the tube. The second end of the agitator is configured to engage the second stop such that the agitator is at a substantially fixed lengthwise position of the tube between the first stop and the second stop. The second stop may be a collar affixed to inner wall of the tube. The second stop may be sized to cover less than 20% of the circumference of the inner wall. The second stop may be a protrusion. The protrusion may be formed by an indentation in the tube. The second stop may comprise two or more protrusions.

In one embodiment, the tube has at least one aperture located between the proximal and distal openings. The at least one aperture may be located proximal or distal to the first stop. The at least one aperture may also be located proximal or distal to the second stop. The at least one aperture may be substantially circular. In another embodiment the at least one aperture is shaped as a slot. The at least one aperture may be surrounded by a supporting ring. The supporting ring may be textured or smooth.

In another embodiment, the tube has two or more radially-spaced apertures located at the same distance between the proximal and distal opening. The radially-spaced apertures may be located in rows. There may be 2, 3, 4, or 5 rows. In some embodiments there may be additional rows. In embodiments with two rows, the first row may have a different distance between the proximal and distal openings than the second row.

DESCRIPTION OF THE DRAWINGS

For a fuller understanding of the nature and objects of the invention, reference should be made to the following detailed description taken in conjunction with the accompanying drawings, in which:

FIG. 15 is a perspective view diagram of a device according to another embodiment of the present invention;

FIG. 16b is a wireframe view of the device of FIG. 16a;

FIG. 18b is a diagram of the device of FIG. 18a.

DETAILED DESCRIPTION OF THE INVENTION

Figure 1:
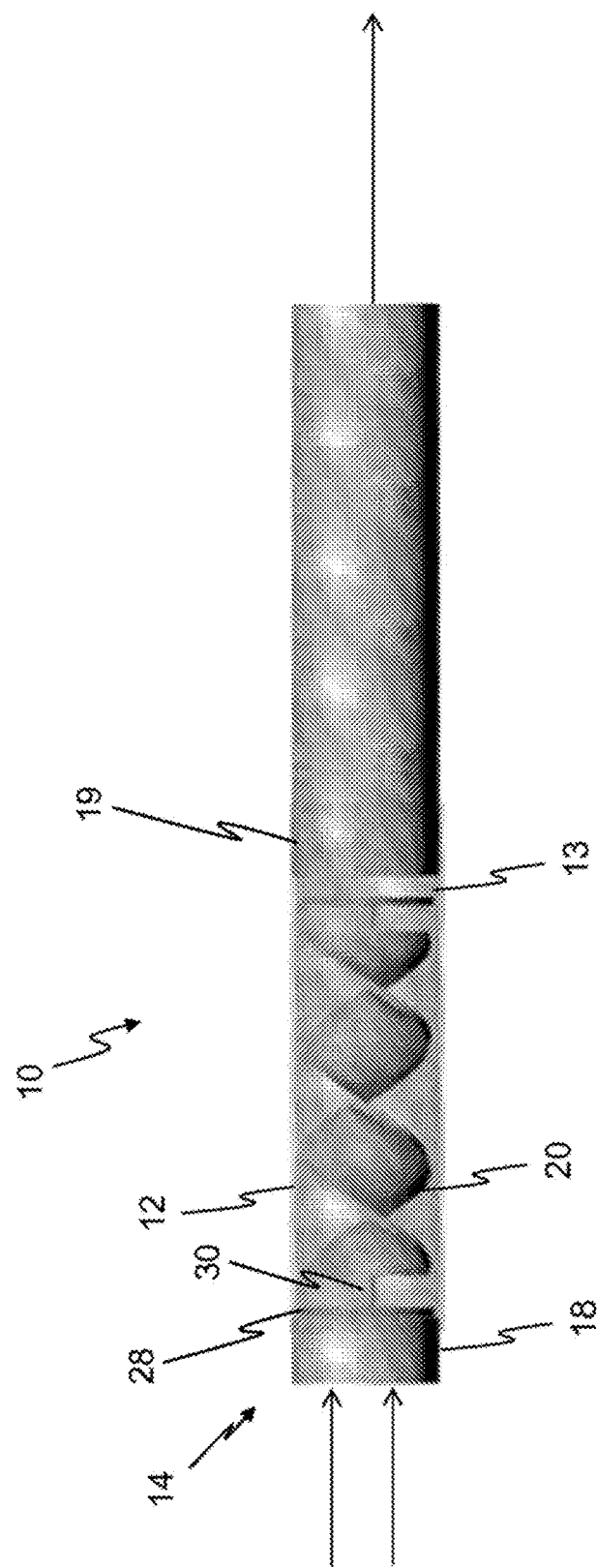
FIG. 1 is a diagram of a device according to an embodiment of the present invention attached to a cannula.

The present invention may be embodied as a device 10 for improving the flow of fluid when applying a vacuum through a suction line. The present invention may also be described as a device 10 for removing viscous and semi-viscous material. The device 10 may comprise a tube 12. The tube 12 may be a suction tube, such as a cannula, commonly used in surgical applications. The tube 12 may be of any diameter appropriate to the application including, for example, 3-4 mm or narrower. The amount of vacuum required to produce adequate suction will depend, at least in part, on the diameter of the tube 12 and other factors described below. The device 10 is scalable for smaller or larger diameter tubes 12.

The tube 12 has a proximal opening 14 and a distal opening 16 (the terms proximal and distal are used herein to describe the location relative to the patient). The proximal opening 14 is configured for suction of fluids from the in-situ fluid location. The distal opening 16 is in pneumatic communication with a vacuum source 90—the vacuum source 90 may or may not make up a part of certain embodiments of the present invention.

The tube 12 of the device 10 includes a first stop 18 at a first lengthwise location on an inner wall 13 of the tube 12. The tube 12 may further comprise a second stop 19 at a second lengthwise location on the inner wall 13. The stops are further described below in relation to an agitator 20 component.

The device 10 comprises an agitator 20 having a first end 22 and a second end 24. The agitator 20 is rotatably disposed in the tube 12. The agitator 20 has a helical blade 26 having an axis 27.

The first end 22 of the agitator 20 is configured to engage with the first stop 18 of the tube 12. In this way, the agitator 20 will be prevented from longitudinal movement beyond the first stop 18 of the tube 12. The first stop 18 and the first end 22 are configured such that the agitator 20 will be prevented from longitudinal movement beyond the first stop 18 while being rotatable about a primary longitudinal axis within the tube 12. The first stop 18 may be a ring (e.g., a collar) on the inner wall 13 of the tube 12. For example, a collar may be affixed to the inner wall 13. The first end 22 may be an end of the helical blade 26. In this manner, the first end 22 (end of the helical blade 26) of the agitator 20 may slidingly abut the collar as the agitator 20 rotates around a longitudinal axis.

In another embodiment, the first stop 18 may be a protrusion on the inner wall 13 of the tube 12. The protrusion may make up less than the entire circumference of the inner wall 13. For example, the protrusion may extend around less than 50%, 40%, 30%, 20%, 10%, or less of the circumference of the inner wall 13. The first stop 18 may comprise more than one protrusion. In such embodiments, the agitator 20 may further comprise a cap 28, such as a ring. The cap 28 may be affixed directly to the helical blade 26 of the agitator 20 or the cap 28 may be connected to the helical screw 26 by a connecting rod 30. The cap 28 may be connected to the connecting rod 30 by one or more spokes 32.

Embodiments of the device 10 may further comprise a second stop 19 configured to engage with the second end 24 of the agitator 20. In this way, the agitator 20 may be captured in the tube 12 at a longitudinal position (or a range of positions) between the first stop 18 and the second stop 19, yet the agitator 20 will remain rotatable about a longitudinal axis.

In use, the agitator 20 will be urged to rotate by the flow of fluid through the tube 12 caused by the application of a vacuum at the distal end of the tube 12. In this manner, the agitator 20 can break-up less viscous fluids or even solid matter suctioned into the tube 12, thereby reducing the risk of occlusion of the tube 12 and downstream components.

In another embodiment, the device 50 is configured to be removably attached to a cannula 70, the cannula 70 not making up a part of the device 50 of this embodiment. The device 50 comprises a housing 52 with a proximal opening (similar to the aforementioned proximal opening of the tube 12 above) and a distal opening at a distal end of the housing 52. The distal end is configured for attachment to a cannula 70, such as, for example, those commonly used for suctioning in surgical applications. The device 50 comprises an agitator 54 similar to the agitator described above.

In these embodiments the device 50 comprises a housing 52 that contains an agitator 54. The housing 52 may be made from a translucent material so the user can detect if suction is being reduced due to clogging. The housing 52 may be stiff or slightly flexible. The housing 52 may have one end configured for attachment to a surgical tube 70, such as a cannula. Attachment may be performed through a friction fit, clamping mechanism, or any other attachment known in the art. The diameter of the housing 52 may be larger than that of the tube 70, smaller, or have the same diameter as the tube 70. For embodiments that are configured to attach to the end of a surgical tool, the housing may have stops. In one embodiment, the diameter of the housing is larger than the diameter of the tube and the tube end acts as a stop to prevent the agitator from moving through the tube.

In embodiments where an agitator is built into a surgical tube, the tube may have a stop for maintaining the agitator at a lengthwise position in the tube which is substantially fixed. For example, the stop may be a collar inside the surgical tube that decreases the diameter of the interior of the tube. In this way, the decreased diameter prevents the agitator from travelling longitudinally through the tube when a suction force is applied. In other embodiments, the stop may comprise inward projections from an inner wall of the tube.

In some embodiments there are two stops located at different lengthwise positions in the tube. In these embodiments, the stops prevent the agitator from travelling in either longitudinal direction within the tube—up the surgical tube or from falling out/travelling down the surgical tube.

The stop(s) may be positioned to provide an agitator with a limited amount of longitudinal movement within the housing or tube. For example, the distance between the stops may be greater than the length of the agitator. It may be advantageous to allow limited longitudinal movement of the agitator within the housing or tube. In other embodiments, the stops are placed to prevent the agitator from any longitudinal movement.

The agitator has a first end and a second end located at the longitudinal extents of the agitator. The agitator comprises a helical blade having a primary longitudinal axis. In some embodiments, the agitator may further comprise a central shaft. The agitator may be made from plastic, metal, or other material, or combinations of these. The weight of the agitator may be selected to account for the use of the device (e.g., to affect the rotation and speed of the agitator). For example, the weight may be distributed such that the helical blade is heavier along the primary longitudinal axis, or along the circumference, or any other configuration appropriate to the use.

The helical blade may be smooth or textured. In some embodiments, the helical blade may have surface features configured to break up viscous material.

The agitator may also include a cap, for example, a ring, positioned at the first end. The cap may be configured to engage with the corresponding stop of the tube or housing such that the mechanism cannot move past the stop. The agitator may also include a cap positioned at the second end. The cap may comprise an annular ring connected to the helical blade by a connecting rod and one or more spokes. The spokes may be angled, curved, or any other configuration.

When vacuum is applied to the tube, the helical blade is urged by the flow of fluid (e.g., air, blood, irrigation, or other fluids and combinations) to rotate within the tube. The speed of rotation may be controlled by the amount of vacuum applied, the shape of the helical blade, the construction material, the fluid being moved through the device, etc.

Figure 2:
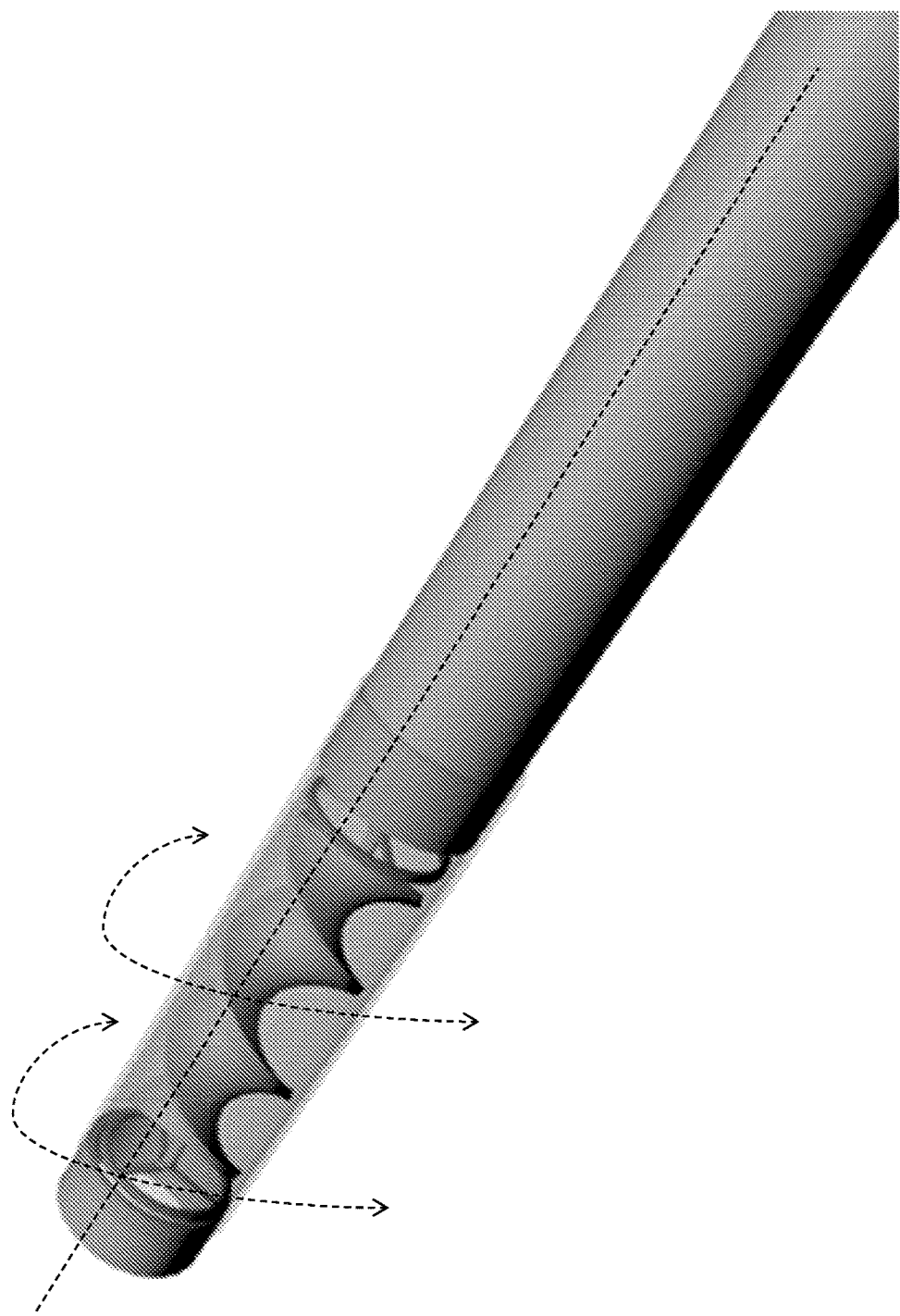
FIG. 2 is a perspective view of the device of FIG. 1 attached to the cannula.
Figure 3:
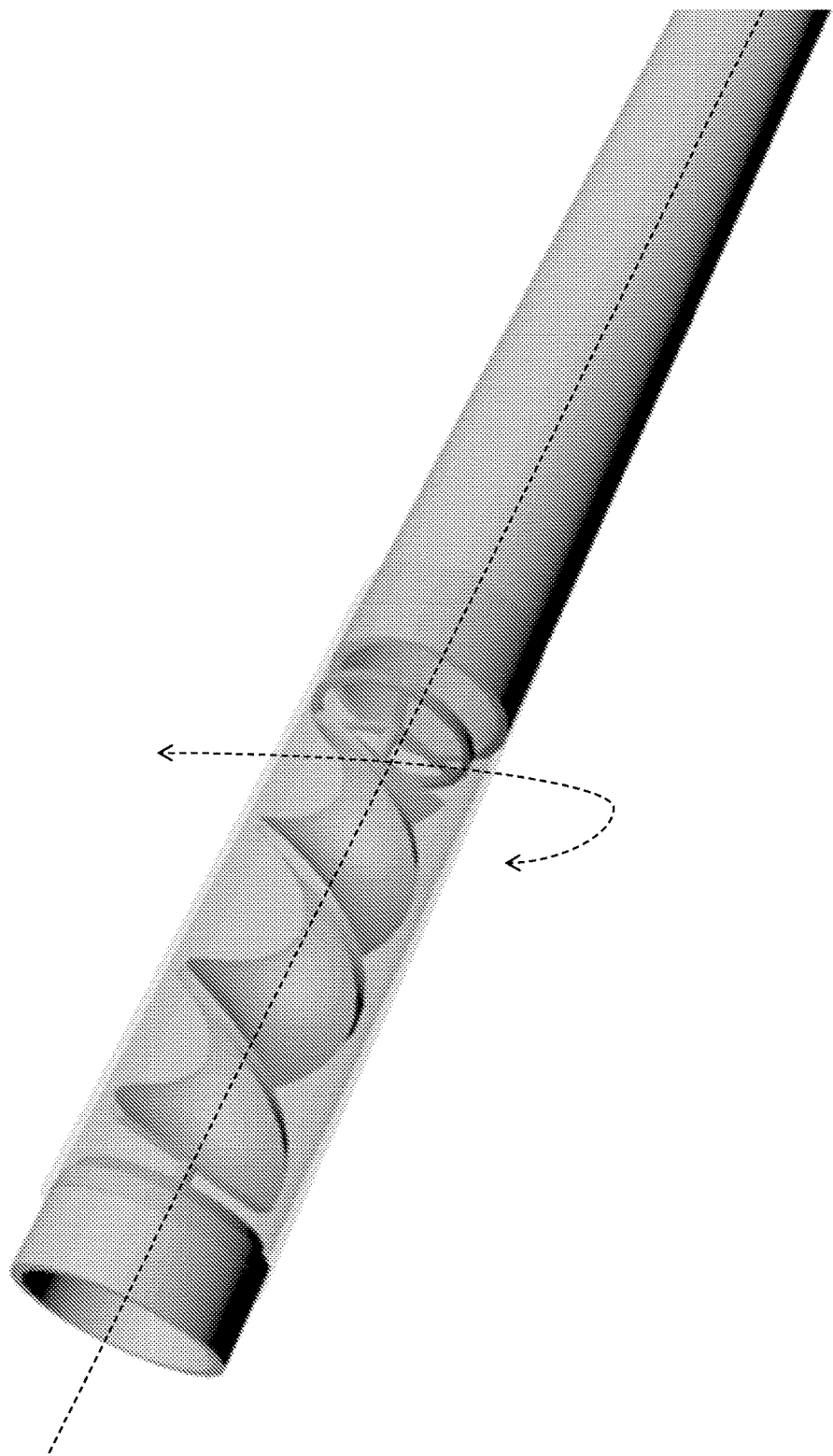
FIG. 3 is another perspective view of the device of FIGS. 1 and 2 attached to the cannula.

The device may also be described as an agitator for flow of fluid by application of a vacuum through a suction line (FIG. 1). In one embodiment of this invention, the device provides suction by applying a vacuum through a single line using conventional suction devices available in the market. One end of the device is attached to a suction cannula. The vacuum causes the agitator to freely rotate thereby circulating and breaking down fluid drawn in at the other end (FIGS. 2 and 3).

Figure 4A:
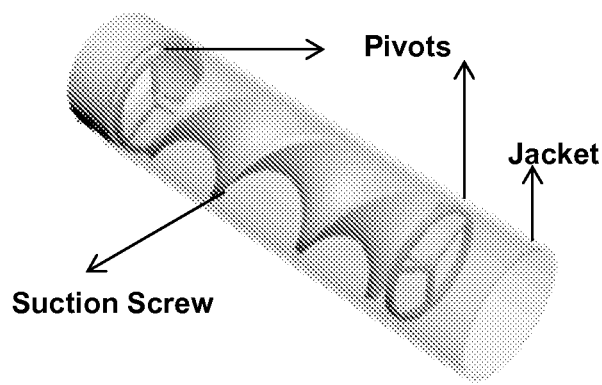
FIGS. 4a and 4b are diagrams of a device according to another embodiment of the present invention showing an agitator in a housing.
Figure 4B:
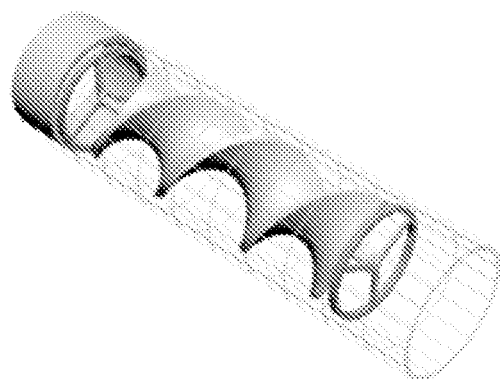
Figure 5A:
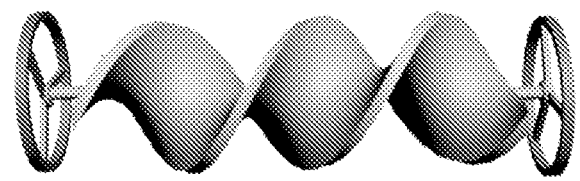
FIGS. 5a, 5b, 5c, and 5d are side-views of an agitator another embodiment of the present invention.
Figure 5B:
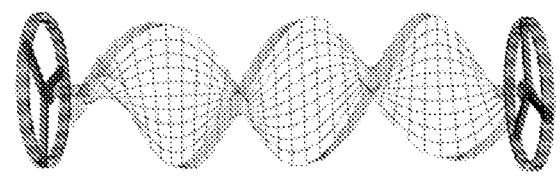
Figure 5C:
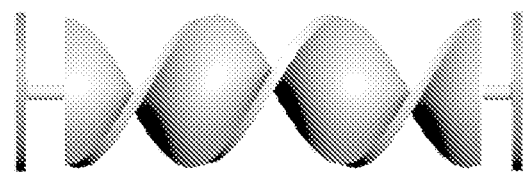
Figure 5D:
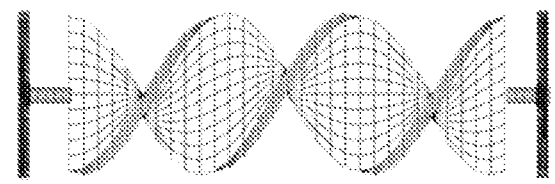

FIGS. 4a and 4b show one embodiment of the present invention which is a device that can be affixed to the end of a surgical tube. In this embodiment, the device has apertures (openings) to allow the passage of viscous and/or non-viscous fluid. Also in this embodiment, the device comprises an agitator with a cap configured as an annular ring which has a larger diameter than the stop in the tube or housing. Two caps are present in the depicted embodiment and the caps are similarly configured. In other embodiments, caps on each end of the agitator may be configured differently from one another. FIGS. 5a-5d show views of an agitator including the helical bade, first end, second end, caps, connecting rods, and spokes.

Figure 6A:
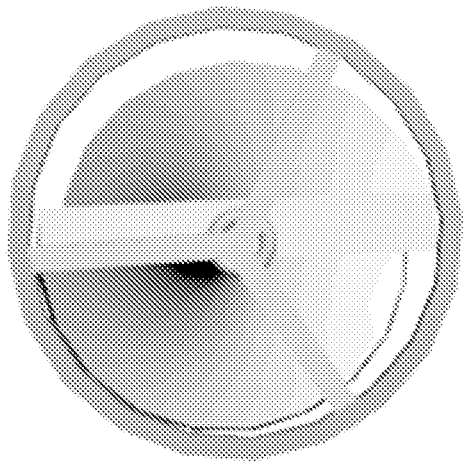
FIGS. 6a and 6b are end-views (along a longitudinal axis) of the agitator of FIGS. 5a-5d.
Figure 6B:
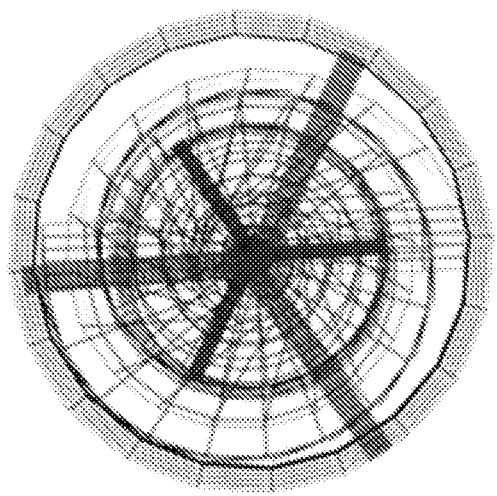

FIGS. 6a and 6b show an end view of one embodiment of the present invention. In this view, the annular ring is connected to the connecting rod by three spokes. In the figures, the helical blade can also be seen in relation to a longitudinal axis of the cap and shaft. Embodiments may or may not be centered along a longitudinal axis of the agitator and/or the tube/housing.

Figure 7:
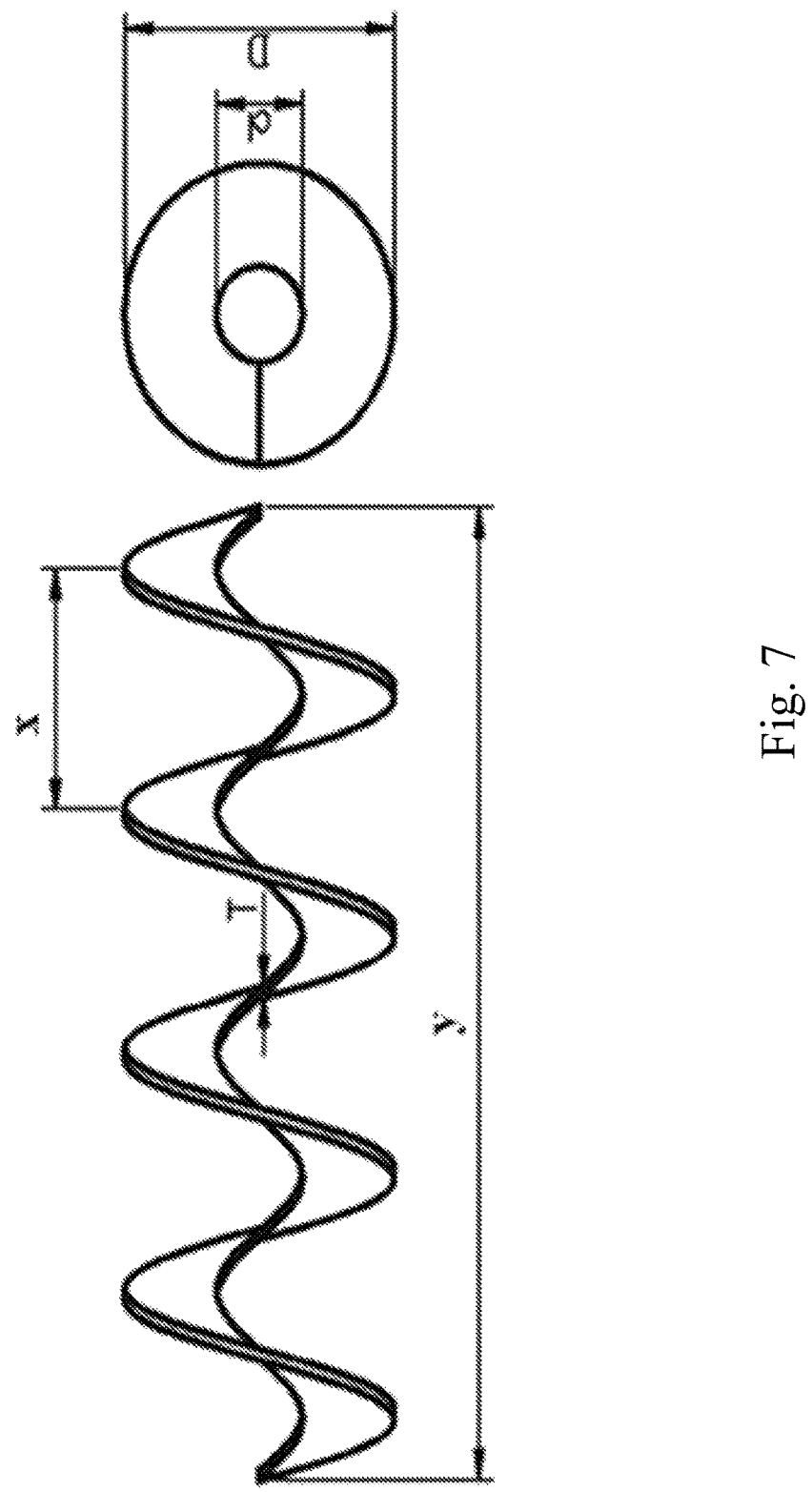
FIG. 7 is a diagram showing an agitator according to another embodiment of the present invention.

FIG. 7 shows a diagram illustrating a helical blade according to another embodiment of the present invention. T denotes the thickness of the helical blade and x denotes the distance between peaks (periodicity) of the helical blade. D denotes the total diameter of the helical blade whereas d denotes the diameter of a central passage of a helical blade of this embodiment. The longitudinal length of the helical blade is denoted by y.

Figure 8:
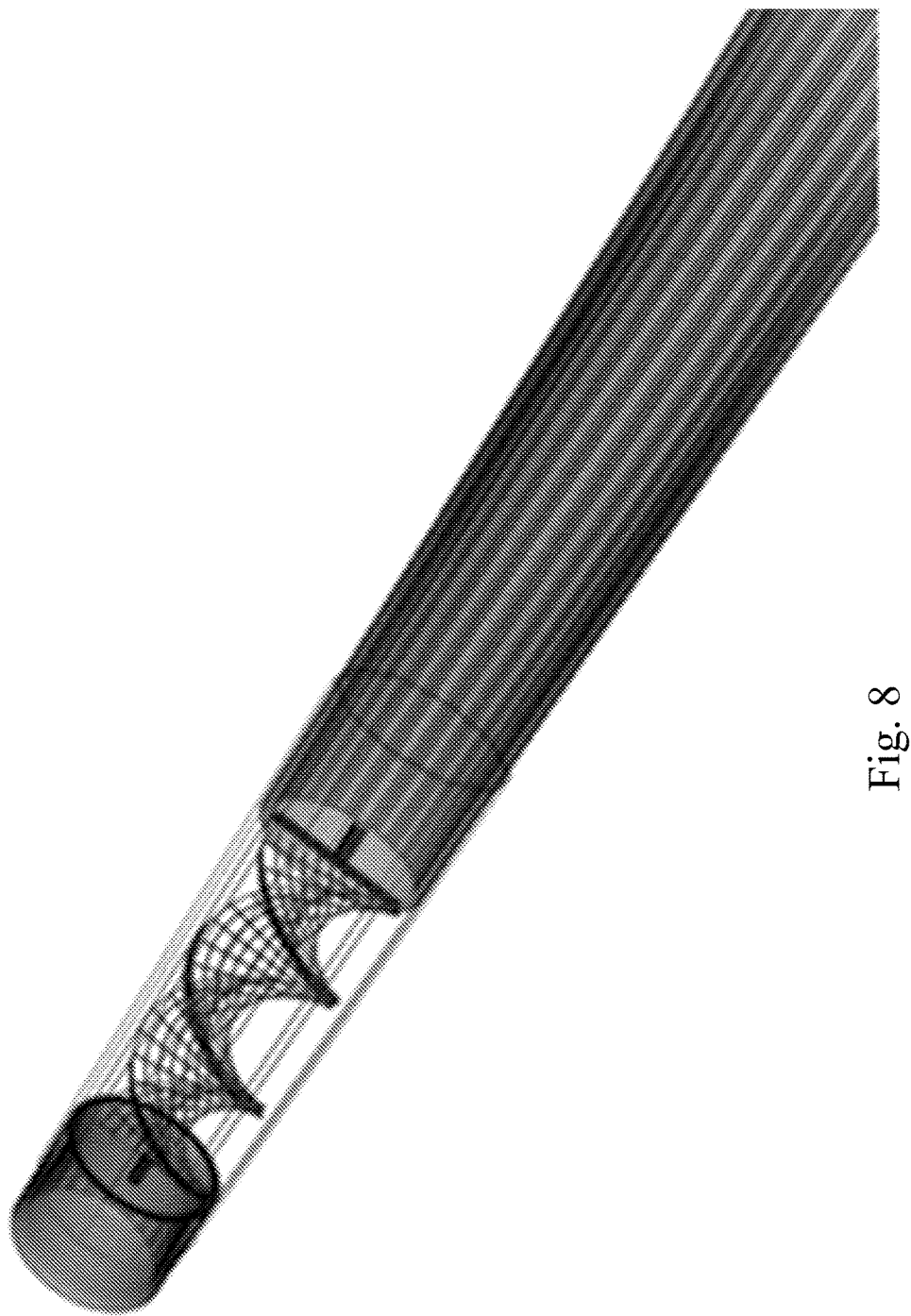
FIG. 8 is a partial wireframe drawing showing a device according to another embodiment of the present invention.
Figure 9:
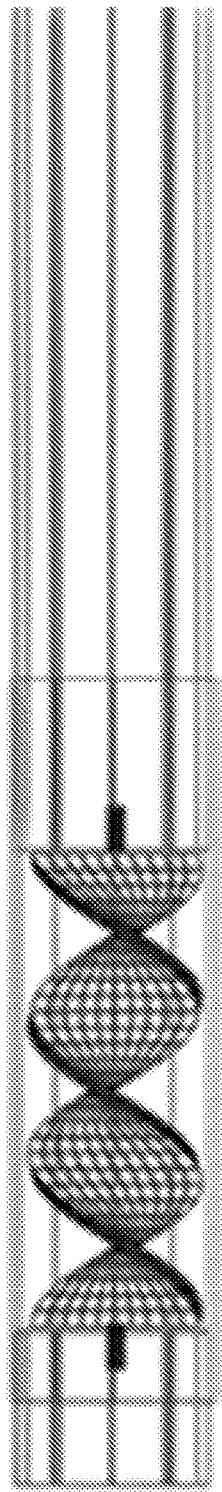
FIG. 9 is a wireframe side view of the device of FIG. 8.

FIGS. 8-9 show another embodiment of a device according to an embodiment of the present invention wherein the device is integrated with the surgical tube (either integrally or by removable attachment). In this embodiment, shafts of the agitator extend longitudinally beyond the extents of the helical blade. The shafts may serve as pivot points for rotation of the agitator (e.g., when used with bearings and/or other structures adapted to rotatably engage the shafts.

Figure 10:
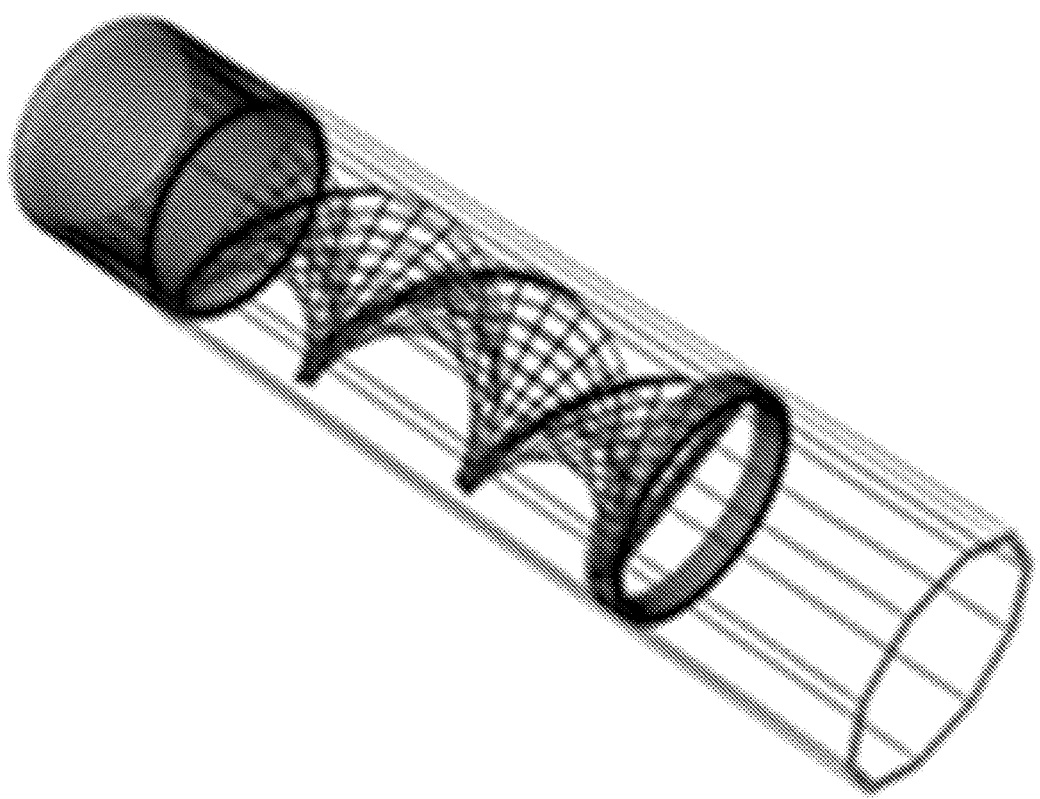
FIG. 10 is a partial wireframe drawing showing a device according to another embodiment of the present invention.
Figure 11:
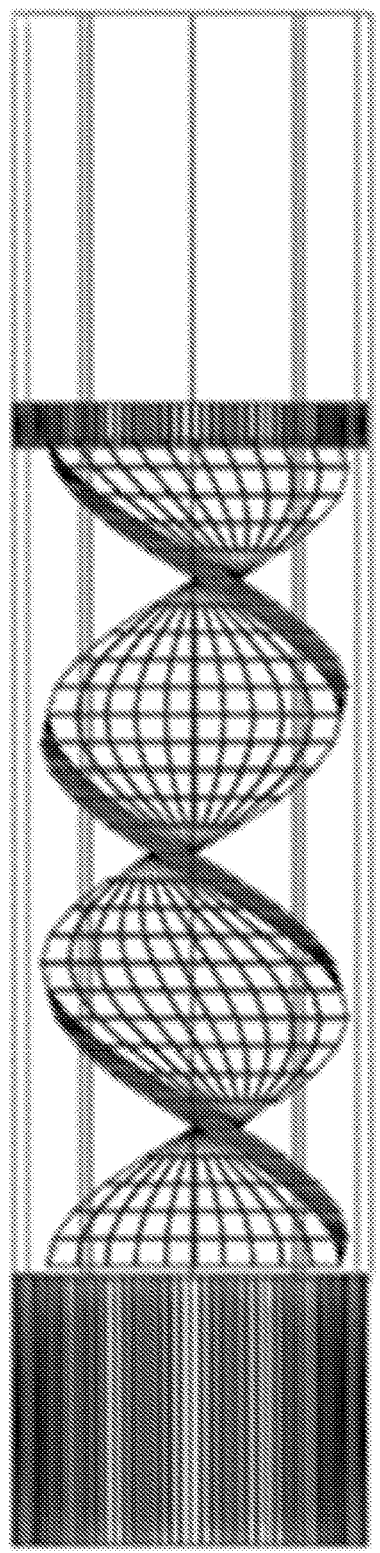
FIG. 11 is a partial wireframe side view of the device of FIG. 10.

FIGS. 10-11 depict an embodiment of a device having an agitator with another embodiment of an end cap.

Figure 12:
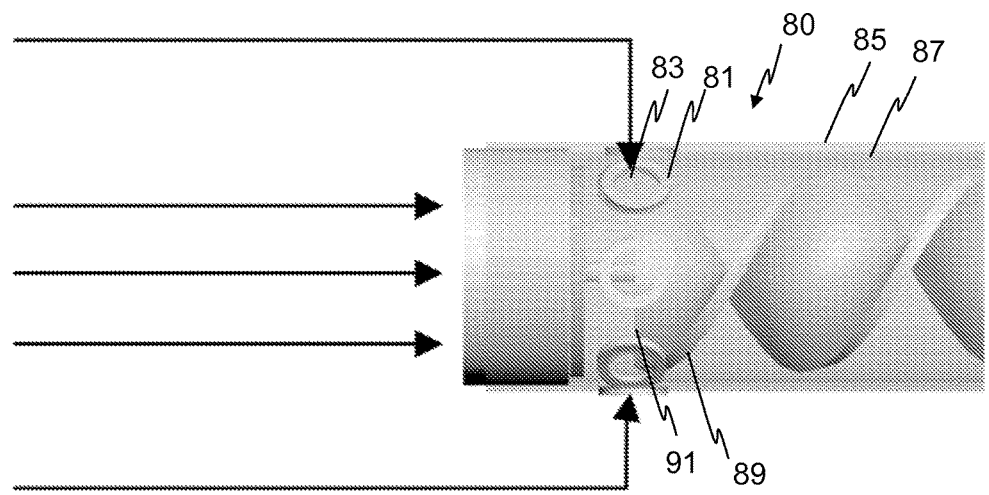
FIG. 12 is a diagram of a device according to another embodiment of the present invention.
Figure 13:
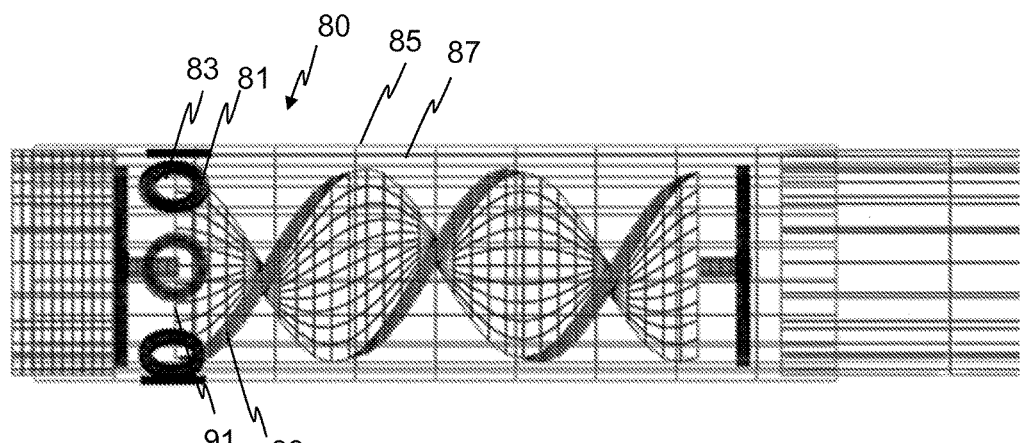
FIG. 13 is a wireframe view of the device of FIG. 13, the device attached to a cannula.
Figure 14:
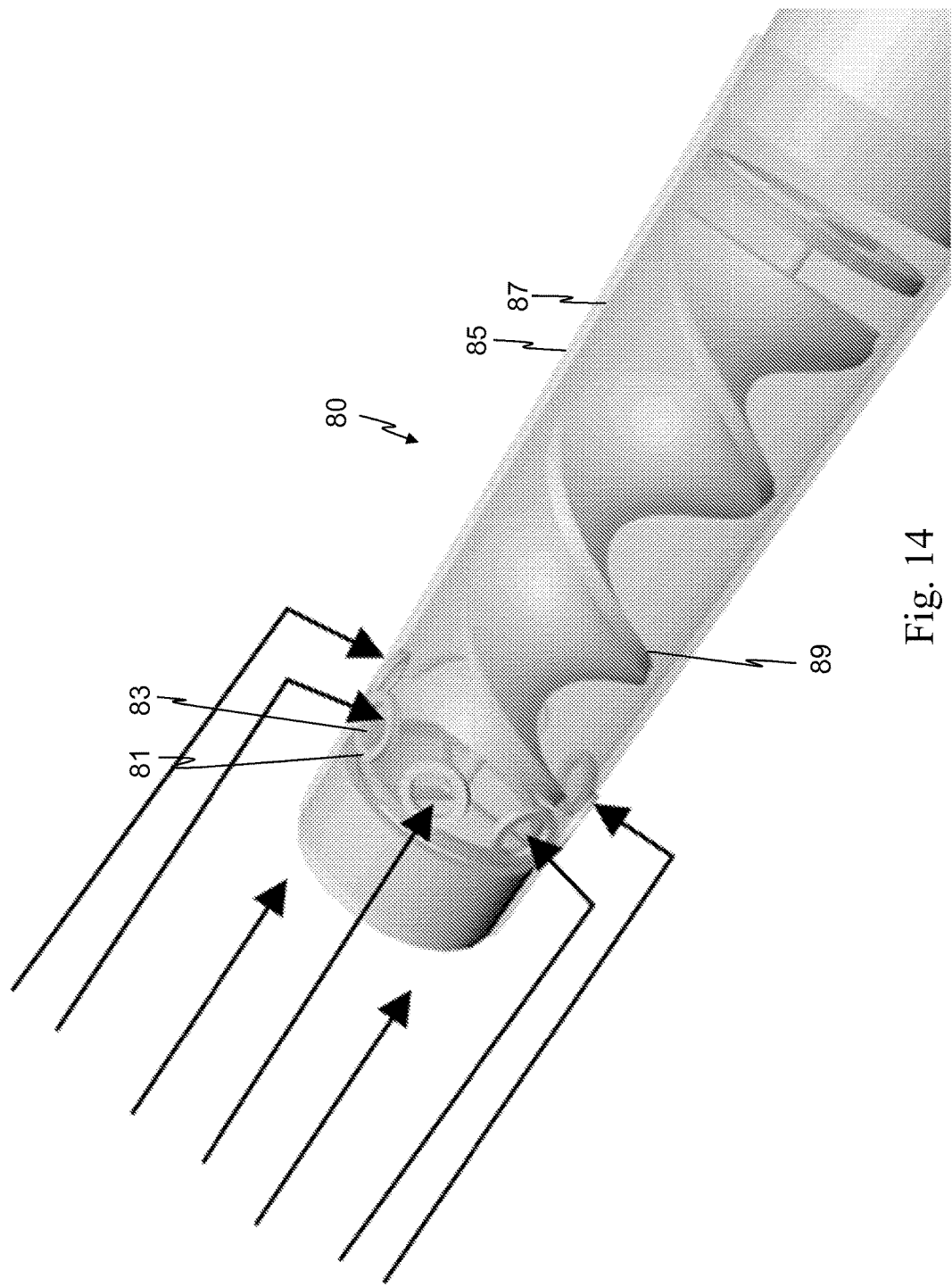
FIG. 14 is a perspective view of the device of FIG. 12 attached to the cannula.

FIGS. 12-14 show another embodiment of a device 80 according to the present invention. Device 80 has a plurality of apertures 83 located on tube 85. The apertures 83 extend through the inner wall 87 of the tube 85. In this embodiment, the apertures 83 are substantially circular. The apertures 83 may be spaced radially around the tube 85. The apertures 83 may be located at the proximal end of the tube 85. In one embodiment, the apertures 83 are located at the proximal end 91 of the agitator 89. The apertures 83 may be located distally or proximally from any point of the agitator 89. The apertures 83 are configured for the suction of fluids from the in-situ fluid location. Each aperture 83 may be surrounded by a reinforcing ring 81. The reinforcing ring 81 may be constructed from the same material as the tube 85 or from a different material. The reinforcing ring 81 may have a smooth or rough texture.

In one embodiment the apertures may be slots. The slots may have a long dimension and a short dimension. The long dimension of the slot may extend radially around the tube. In another embodiment, the long dimension of the slot extends distally or proximally along the tube. In one embodiment, the slot follows a helical path around the tube. The apertures may be both slots and circles. Other shapes may be used for the apertures.

FIG. 15 shows another embodiment of a device 100 according to the present invention. Device 100 has a plurality of apertures 103 located on the tube 105. The apertures 103, 111 extend through the inner wall 107 of the tube 105. In this device 100 there are two rows of radially-spaced apertures 103, 111. The first row of apertures 111 is located proximally on the tube 105. The second row of apertures 103 is located distally on the tube 105. The first row of apertures 111 may be of a different size than the second row of apertures 103. For example, the second row of apertures may have a smaller size.

Figure 16A:
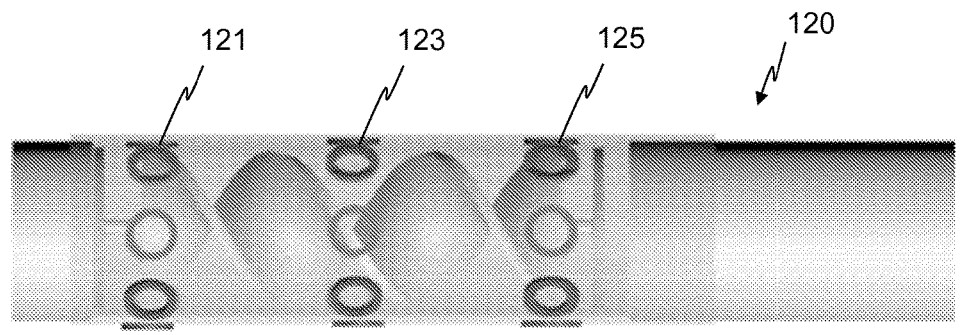
FIG. 16a is a diagram of a device according to another embodiment of the present invention.
Figure 16B:
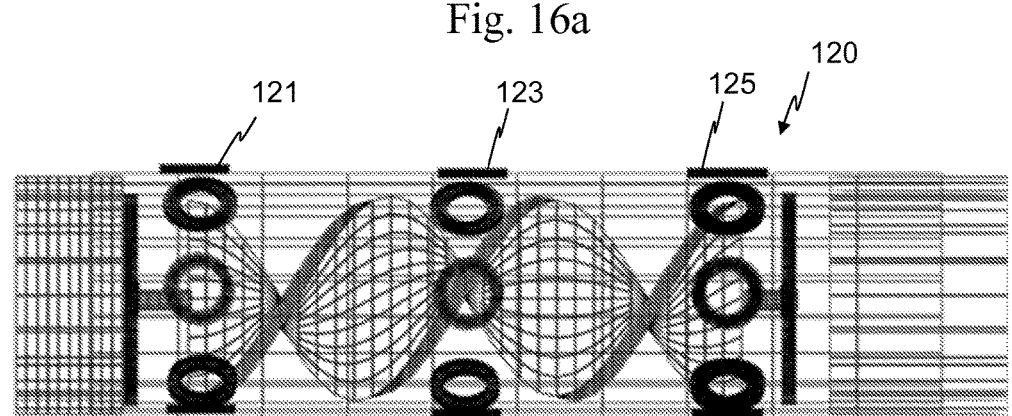

FIGS. 16a-b show another embodiment of a device 120 according to the present invention. In this device 120 there are three rows of radially-spaced apertures. The first row 121 is located proximally on the tube. The second row 123 is located between the first row 121 and the third row 125. The third row 125 is located distally on the tube.

Figure 17:
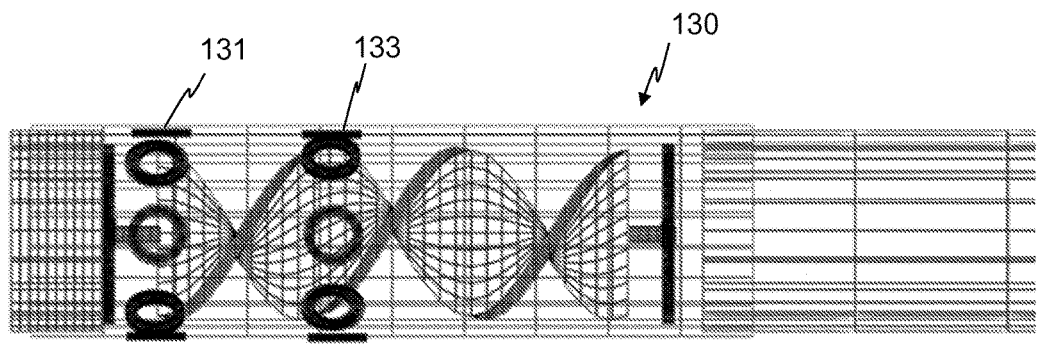
FIG. 17 is a wireframe diagram of a device according to another embodiment of the present invention.

FIG. 17 shows another embodiment of a device 130 according to the present invention. In this device 130 there are two rows of radially spaced apertures. The first row 131 is located proximally on the tube. The second row 133 is located distally on the tube.

Figure 18A:
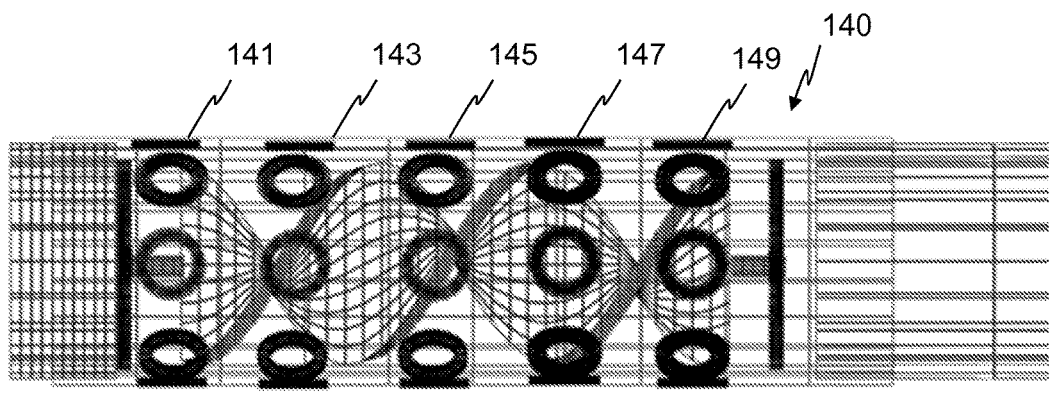
FIG. 18a is a wireframe diagram of a device according to another embodiment of the present invention.
Figure 18B:
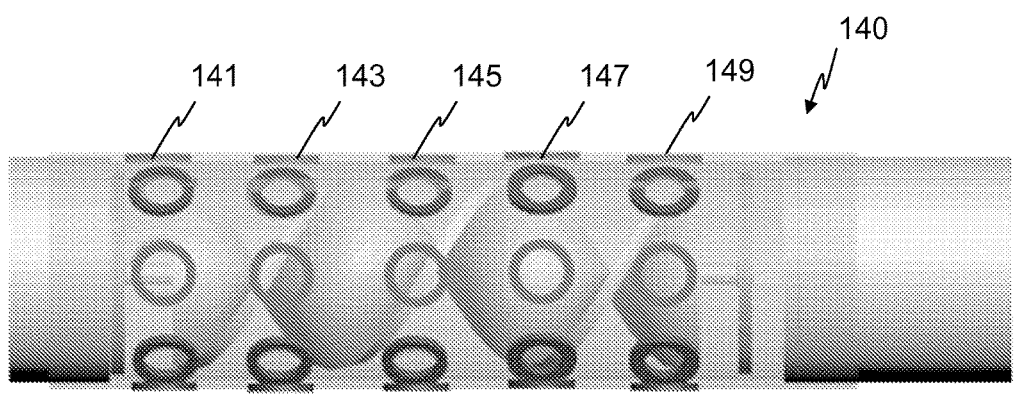

FIGS. 18a-b show another embodiment of device 140 according to the present invention. In this device 140 there are five rows 141, 143, 145, 147, 149 of radially-spaced apertures along the tube. The rows are evenly spaced along the length of the tube.

One exemplary embodiment is a device for removing viscous or semi-viscous material from an individual using suction provided by a vacuum source. The device comprises: a tube having a proximal opening, a distal opening in pneumatic communication with the vacuum source, and a first stop at a first lengthwise position on an inner wall of the tube; and an agitator rotatably disposed in the tube, the agitator having a helical blade, a first end, and a second end, and the first end is configured to engage the first stop such that the agitator is rotatable about the axis of the helical blade while being at a substantially fixed position along the length of the tube.

In one embodiment, the tube has at least one aperture in a wall of the tube located between the proximal and distal openings. In another embodiment, the at least one aperture is located proximal to the first stop. In one embodiment, the at least one aperture is located distal to the first stop. In another embodiment, the at least one aperture is substantially circular. In one embodiment, the at least one aperture is a slot. In another embodiment, the at least one aperture is surrounded by a supporting ring. In another embodiment, the tube has two or more radially-spaced apertures located at the same distance between the proximal and distal opening. In one embodiment, the tube has two or more radially-spaced apertures located in a first row and a second row, the first row having a different distance between the proximal and distal openings than the second row.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A device for removing viscous or semi-viscous material from an individual using suction provided by a vacuum source, the device comprising: a tube having a proximal opening, a distal opening in pneumatic communication with the vacuum source, and a first stop at a first lengthwise position on an inner wall of the tube; an agitator rotatably disposed in the tube, the agitator having a helical blade, a first end, and a second end, and the first end is configured to engage the first stop such that the agitator is rotatable about the axis of the helical blade while being at a substantially fixed position along the length of the tube; wherein the first end of the agitator is configured as a ring.

2. The device of claim 1, wherein the first stop is a collar affixed to the inner wall of the tube.

3. The device of claim 1, wherein the first stop is a protrusion.

4. The device of claim 3, wherein the protrusion is formed by an indentation in the tube.

5. The device of claim 1, wherein the first stop comprises two or more protrusions.

6. The device of claim 1, wherein the first stop is sized to cover less than 20% of the circumference of the inner wall.

7. The device of claim 1, wherein the ring is connected to the helical blade by way of a connecting rod.

8. The device of claim 1, wherein the tube has a second stop at a second lengthwise position on the inner wall of the tube and the second end of the agitator is configured to engage the second stop such that the agitator is at a substantially fixed lengthwise position of the tube between the first stop and the second stop.

9. The device of claim 8, wherein the second stop is a collar affixed to the inner wall of the tube.

10. The device of claim 8, wherein the second stop is a protrusion.

11. The device of claim 10, wherein the protrusion is formed by an indentation in the tube.

12. The device of claim 8, wherein the second stop comprises two or more protrusions.

13. The device of claim 8, wherein the second stop is sized to cover less than 20% of the circumference of the inner wall.

14. The device of claim 13, wherein the second end of the agitator is configured as a ring.

* * * * *